United States Patent [19]

George et al.

[11] Patent Number: 5,420,130

[45] Date of Patent: May 30, 1995

[54] 2-AMINOPYRAZINE-5-CARBOXAMIDE DERIVATIVES, THEIR PREPARATION AND THEIR APPLICATION IN THERAPEUTICS

[75] Inventors: Pascal George, St Arnoult en Yvelines; Benoit Marabout, Massy; Jacques Froissant, Morée, all of France

[73] Assignee: Synthelabo, Le Plessis Robinson, France

[21] Appl. No.: 243,315

[22] Filed: May 16, 1994

[30] Foreign Application Priority Data

May 17, 1993 [FR] France .................. 93 05930

[51] Int. Cl.$^6$ .................. A61K 31/495; C07D 241/28; C07D 401/12; C07D 403/12
[52] U.S. Cl. .................... 514/252; 514/255; 544/295; 544/357; 544/373; 544/392; 544/407; 546/201; 546/232; 564/316; 564/354
[58] Field of Search ............. 544/295, 357, 407; 514/252, 255

[56] References Cited

U.S. PATENT DOCUMENTS 4,041,032  8/1977  Murakami et al. .................. 544/407
5,164,397  11/1992  George et al. .................. 514/275

*Primary Examiner*—Emily Bernhardt

*Attorney, Agent, or Firm*—Jacobson, Price, Holman & Stern

[57] ABSTRACT

Compounds corresponding to the general formula (I)

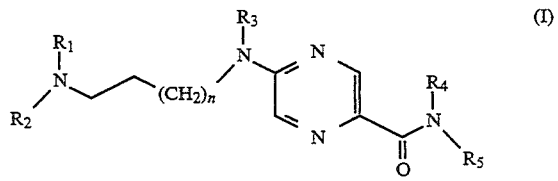

in which n represents 0 or 1, $R_1$ represents a methyl group, in which case $R_2$ represents a phenoxy($C_1$-$C_4$)alkyl group (in which the phenoxy group is optionally substituted), or else $R_1$ and $R_2$ together form, and with the nitrogen atom which carries them, a 4-(phenoxymethyl)piperid-1-yl group (in which the phenoxy group is optionally substituted) or a 4-phenylpiperazin-1-yl group (in which the phenyl group is optionally substituted), $R_3$ represents a hydrogen atom or a methyl group, $R_4$ represents a hydrogen atom and $R_5$ represents a hydrogen atom or a group of general formula -$CH_2$-$CH_2$-NH-$R_6$, $R_6$ being a hydrogen atom or a tert-butyloxycarbonyl, 4-carbamoylpyrimidin-2-yl or 5-carbamoylpyrazin-2-yl group, are useful in the treatment of diseases and complaints involving hyperactivity of the α-adrenergic system at the level of the lower urinary apparatus.

5 Claims, No Drawings

2-AMINOPYRAZINE-5-CARBOXAMIDE DERIVATIVES, THEIR PREPARATION AND THEIR APPLICATION IN THERAPEUTICS

The subject of the present invention is 2-aminopyrazine-5-carboxamide derivatives, their preparation and their application in therapeutics.

The compounds of the invention correspond to the general formula (I)

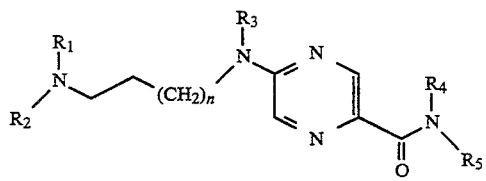

in which
n represents the number 0 or 1,
$R_1$ represents a methyl group, in which case
$R_2$ represents a phenoxy($C_1$–$C_4$)alkyl group (in which the phenoxy group optionally carries 1 or 2 substituents chosen from halogen atoms and methoxy and ethoxy groups), or else $R_1$ and $R_2$ together form, and with the nitrogen atom which carries them, a 4-(phenoxymethyl)piperid-1-yl group (in which the phenoxy group optionally carries 1 or 2 $C_1$–$C_4$ alkyl groups) or a 4-phenylpiperazin-1-yl group (in which the phenyl group optionally carries 1 or 2 substituents chosen from halogen atoms and methoxy and ethoxy groups and cyclopropyl and $C_1$–$C_4$ alkyl groups),
$R_3$ represents a hydrogen atom or a methyl group,
$R_4$ represents a hydrogen atom,
$R_5$ represents a hydrogen atom or a group of general formula

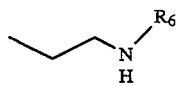

$R_6$ being a hydrogen atom, a tert-butyloxycarbonyl group, a 4-carbamoylpyrimidin-2-yl group or a 5-carbamoylpyrazin-2-yl group.

The compounds of the invention can exist in the form of bases or of addition salts with acids.

In accordance with the invention, the compounds of general formula (I) can be prepared by a process illustrated in the following scheme.

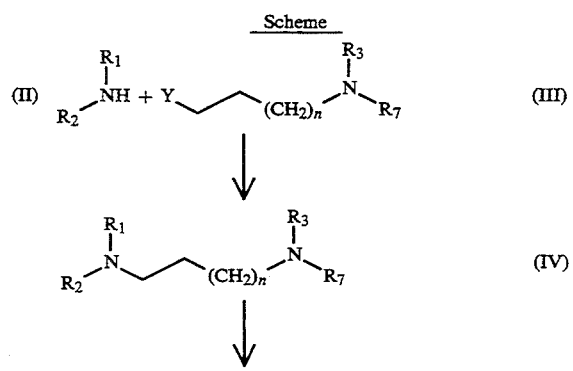

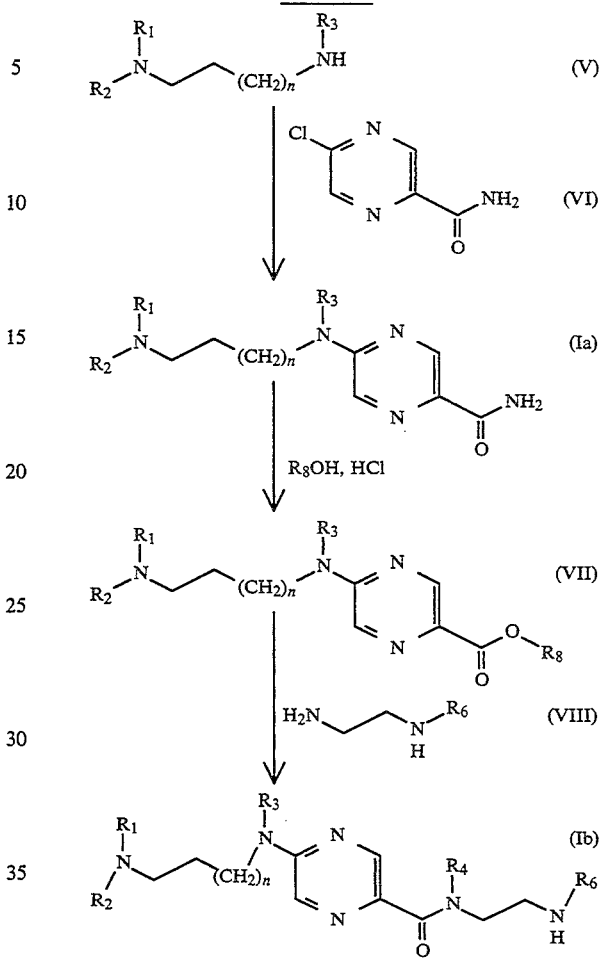

An amine of general formula (II) in which $R_1$ and $R_2$ are as defined above, optionally in the salt form, is reacted with a halogenated reactant of general formula (III) in which Y represents a halogen atom, n is as defined above and either $R_3$ is as defined above and $R_7$ represents a protective group of the amine, for example a triphenylmethyl group, or $R_3$ and $R_7$ together form, and with the nitrogen atom which carries them, a phthalimido group, as described in J. Med. Chem., (1989), 32(8), 1921–1926.

The reaction is carried out in an aprotic solvent such as dimethylformamide, in the presence of an inorganic base such as potassium carbonate, at a temperature of 40° to 80° C.

A diamine of general formula (IV) is obtained, the end alkylamine of which is deprotected: in the case where $R_7$ is a triphenylmethyl group, a treatment with gaseous hydrochloric acid in an aliphatic alcohol, for example methanol, at a temperature of 0° to 60° C. is carried out; in the case where $R_3$ and $R_7$ together form a phthalimido group, a treatment analogous to that described in the literature mentioned above, for example with hydrazine, is carried out.

An amine of general formula (V) is obtained, which is reacted with 2-chloropyrazine-5-carboxamide of formula (VI) in an aprotic solvent, for example N,N-dimethylformamide, in the presence of a base, for example potassium carbonate, at a temperature of 20° to 40° C., in order to arrive at the 2-aminopyrazine-5-carboxamide derivative of general formula (Ia) which corresponds to the general formula (I) when $R_4$ and $R_5$ each represent a hydrogen atom.

In order to prepare the compounds of general formula (I) in which $R_5$ represents a group of general formula

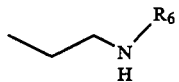

an amide of general formula (Ia), in which n, $R_1$, $R_2$ and $R_3$ are as defined above, is converted to an ester of general formula (VII) in which $R_8$ represents a $C_1$–$C_4$ alkyl group by reaction with a $C_1$–$C_4$ aliphatic alcohol, for example methanol, in the presence of an acid, for example gaseous hydrochloric acid, at a temperature of 0° to 60° C., and then the ester thus obtained is reacted with a diamine of general formula (VIII) in which $R_6$ represents a protective group of the amine, for example a tert-butyloxycarbonyl group, in an aliphatic alcohol, for example methanol or n-butanol, at a temperature of 0° to 100° C., in order to obtain a compound of general formula (Ib) in which $R_6$ represents a tert-butyloxycarbonyl group.

In order to prepare the compounds of general formula (Ib) in which $R_6$ represents a 4-carbamoylpyrimidin-2-yl or 5-carbamoylpyrazin-2-yl group, the compound obtained above is deprotected according to a known method, for example with trifluoroacetic acid in dichloromethane, in order to obtain the compound of general formula (Ib) where $R_6$ represents hydrogen, and the latter is reacted with 2-chloropyrimidine-4-carboxamide or 2-chloropyrazine-5-carboxamide, in an aprotic solvent, for example N,N-dimethylformamide, in the presence of a base, for example potassium carbonate, at a temperature of 20° to 40° C.

The amines of general formula (II) can be prepared by methods analogous to those described in Bull. Soc. Chim., (1959) 839–849 in the case of the phenoxyalkylamines, J. Med. Chem., (1987) 30(1), 222–5 and Patent DE-2,737,630 in the case of the phenoxymethylpiperidines.

The halogenated reactant of general formula (III) is either commercially available, when $R_3$ and $R_7$ together form a phthalimido group, or, when $R_3$ represents H or $CH_3$, can be prepared by a method analogous to that described in Patent Application FR-2,656,609.

2-Chloropyrazine-5-carboxamide of formula (VI) can be prepared by a method analogous to that described in J. Her. Chem., 1974, 11, 607–610, Agric. Biol. Chem., 1982, 46(8), 2169–2172, Coll. Czech. Chem. Comm., 1990, 50, 2493–2501 and Coll. Czech. Chem. Comm., 1972, 37, 862–867.

2-Chloropyrimidine-4-carboxamide can be prepared by a method analogous to that described in Patent Application FR-2,656,609.

Monoprotected diamines of general formula (VII) can be prepared by methods analogous to those described in Synthesis (1990), 366–368.

The following examples illustrate in detail the preparation of some compounds according to the invention. The elemental microanalyses and the IR and NMR spectra confirm the structures of the compounds obtained.

The numbers shown between brackets in the titles correspond to those of the first column of the table given later.

EXAMPLE 1 (COMPOUND NO. 1)

2-[[3-[[2-(2-Methoxyphenoxy)ethyl]methylamino]-propyl]amino]pyrazine-5-carboxamide (E)-but-2-enedioate (1:1)

1.1.
N-[2-(2-Methoxyphenoxy)ethyl]-N-methyl-N'-(triphenylmethyl)-1,3-propanediamine 8.05 g (0.0370 mol) of N-methyl-2-(2-methoxyphenoxy) ethylamine hydrochloride, 15.5 g (0. 0407 mol) of N-triphenylmethyl-3-bromopropylamine, (0.0925 mol) of potassium carbonate and 75 ml of N,N-dimethylformamide are introduced, under argon, into a 500 ml, three-necked, round-bottomed flask. The mixture is stirred for 15.5 h at 90° C. The reaction mixture is treated with a mixture of water and ice and extracted with ethyl acetate. The organic phase is washed with water, dried over sodium sulphate and concentrated under reduced pressure.

There are obtained 18.2 g of an orange oil which is purified by chromatography on silica gel, the eluent being a 98/2 mixture of dichloromethane/methanol. There are obtained 13.7 g of oil which is used as is in the following stage.

1.2.
N-[2-(2-Methoxyphenoxy)ethyl]-N-methyl-1,3-propanediamine 12.9 g (0.0268 mol) of N-[2-(2-methoxyphenoxy)ethyl]-N-methyl-N'-(triphenylmethyl)-1,3-propanediamine and 250 ml of methanol are introduced into a 1 l round-bottomed flask. A stream of gaseous hydrochloric acid is passed for 15 min while cooling with a mixture of water and ice. The mixture is allowed to return to room temperature and is then brought to the reflux temperature for 7.5 h. The mixture is concentrated to dryness and the residue is taken up in ethanol and concentrated again. The residue is taken up in water, the mixture is basified, the supernatant oil is taken up in dilute hydrochloric acid and extraction is carried out with diethyl ether. The acidic aqueous phase is then treated with sodium hydroxide until the pH is basic and extraction is carried out with dichloromethane. The organic phase is washed with water, dried over sodium sulphate and concentrated under reduced pressure. There are obtained 5.6 g of a yellow oil which is used as is in the following stage.

1.3.2-[[3-[[2-(2-Methoxyphenoxy)ethyl]methylamino]-propyl]amino]-pyrazine-5-carboxamide (E)-but-2-enedioate.

5.0 g (0.021 mol) of N-[2-(2-methoxyphenoxy)ethyl]-N-methyl-1,3-propanediamine, 3.3 g (0,021 mol) of 2-chloropyrazine-5-carboxamide, 100 ml of acetonitrile and a few crystals of sodium iodide are introduced, under argon, into a 250 ml round-bottomed flask. 2.9 g (0.021 mol) of potassium carbonate are added and the mixture is heated at the reflux temperature for 30 h.

The mixture is cooled to room temperature, the precipitate is collected by filtration and is purified by chromatography on a column of silica gel, the eluent being a 100/0 to 90/10 dichloromethane/methanol mixture.

The solid obtained is recrystallized from acetonitrile and 2.82 g (0.00785 mol) of base are obtained.

The fumarate is prepared from 2.82 g of base dissolved in 50 ml of methanol by addition of 0.91 g (0.00785 mol) of fumaric acid in solution in 50 ml of methanol. The solution is concentrated under reduced pressure and recrystallization is carried out from ethanol. 3.32 g of white solid are obtained.

Melting point: 161°–163° C.

EXAMPLE 2. (COMPOUND NO. 3)

2-[[3-[4-[[5-Methyl-2-(1-methylethyl)phenoxy]methyl]-piperid-1-yl]propyl]amino]pyrazine-5-carboxamide hydrochloride (1:1)

2.1.

2-[3-[4-[[5-Methyl-2-(1-methylethyl)phenoxy]methyl]-piperid-1-yl]propyl]-1H-isoindole-1,3(2H)-dione 11.35 g (0.04 mol) of 4-[[5-methyl-2-(1methylethyl)-phenoxy]methyl]piperidine hydrochloride, 10.72 g (0.04 mol) of 2-(3-bromopropyl)-1H-isoindole-1,3(2H)-dione and 13.8 g (0.1 mol) of potassium carbonate are reacted in 113 ml of N,N-dimethylformamide. The mixture is stirred for 3 h at 100° C. It is poured into ice-cold water. The solution is extracted with ethyl acetate and it is washed with water. The organic phase is dried over sodium sulphate, filtered and concentrated under reduced pressure. The product obtained is used as is in the following stage.

2.2

4-[[5-Methyl-2-(1-methylethyl)phenoxy]methyl]piperidine-1-propylamine 17.35 g (0.04 mol) of 2-[3-[4-[[5-methyl-2-(1-methylethyl)phenoxy]methyl]piperid-1-yl]propyl]-1H-isoindole-1,3 (2H)-dione are reacted in 340 ml of ethanol with 3.9 ml (0.08 mol) of hydrazine hydrate. The mixture is heated at the reflux temperature for 3 h. The mixture is filtered, the solid being rinsed with a small amount of ethanol, the filtrate is concentrated and taken up in diethyl ether. An insoluble material is again removed by filtration and the filtrate is again concentrated. The insoluble materials are combined in a round-bottomed flask and 25 ml of concentrated hydrochloric acid and 75 ml of water are added. The mixture is brought to reflux for 2 h while stirring. It is allowed to cool, the insoluble material is removed by filtration, rinsing is carried out with water, basification is carried out with concentrated aqueous ammonia and extraction is carried out three times with diethyl ether. The organic phase is dried over sodium sulphate, filtered and concentrated under reduced pressure. A compound is obtained which is used as is in the following stage.

2.3.2-[[3-[4-[[5-Methyl-2-(1-methylethyl)phenoxy]methyl]piperid-1-yl]propyl]amino]pyrazine-5-carboxamide hydrochloride (1:1)

7.45 g (0.0245 mol) of 4-[[5-methyl-2-(1-methylethyl)-phenoxy]methyl]piperidine-1-propylamine, 3.86 g (0.0245 mol) of 2-chloropyrazine-5-carboxamide and 3.38 g (0.0246 mol) of potassium carbonate are reacted in 100 ml of acetonitrile. The mixture is heated for 28 h at the reflux temperature, is then allowed to cool to room temperature and the solvent is evaporated under reduced pressure.

The solid obtained is purified by chromatography on a column of silica gel, the eluent being a 100/0 to 80/20 dichloromethane/methanol mixture. The solid obtained is recrystallized from ethyl acetate and 1.07 g (0.0025 mol) of base are obtained.

The hydrochloride is prepared from 1.07 g of base in solution in 20 ml of 2-propanol by addition of 25 ml of 0.1N hydrochloric acid in 2-propanol and then the solvent is evaporated under reduced pressure. The residue is recrystallized from 2-propanol in order to finally obtain 0.7 g of white solid.

Melting point: 218°–220° C.

EXAMPLE 3 (COMPOUND NO. 5)

2-[[2-[4-(2-Methoxyphenyl)piperazin-1-yl]ethyl]amino]-pyrazine-5-carboxamide (E)-but-2-enedioate (1:1)

3.1.

2-[4-(2-Methoxyphenyl)piperazin-1-yl]-N-(triphenylmethyl)ethanamine 10 g (0.273 mol) of 2-bromo-N-(triphenylmethyl)ethanamine, 200 ml of acetonitrile, 5.15 g (0.0273 mol) of 1-(2-methoxyphenyl)piperazine, 5.6 g of anhydrous potassium carbonate, a few grains of sodium iodide and 1 ml of dimethylformamide are introduced into a 500 ml round-bottomed flask equipped with a reflux condenser and placed under nitrogen. The mixture is heated at reflux for 15 h, the solvents are evaporated, water and dichloromethane are added, the organic phase is separated, washed with water, dried over sodium sulphate and the solvent is evaporated under reduced pressure. A viscous oil is obtained which is purified by chromatography on a column of silica gel, the eluent being a mixture of ethyl acetate and dichloromethane. There are isolated 9.24 g of product which is used as is in the following stage.

3.2. 2-[4-(2-Methoxyphenyl)piperazin-1-yl]ethanamine trihydrochloride 9.24 g of 2-[4-(2-methoxyphenyl)piperazin-1-yl]-N-(triphenylmethyl)ethanamine are dissolved in 400 ml of methanol and, after homogenization, a stream of gaseous hydrochloric acid is passed into the solution for 10 min. The precipitate is collected, rinsed with methanol and dried under vacuum. 5.33 g of white solid are obtained.

3.3 2-[[2-[4-(2-Methoxyphenyl)piperazin-1-yl]ethyl]amino]-pyrazine-5-carboxamide (E)-but-2-enedioate 5.7 g (0.0242 mol) of 2-[4-(2-methoxyphenyl)-piperazin-1-yl]ethanamine, 3.82 g (0.0242 mol) of 2-chloropyrazine-5-carboxamide, 200 ml of acetonitrile and 3.35 g (0.0242 mol) of sodium carbonate are introduced into a 500 ml round-bottomed flask equipped with a reflux condenser and placed under nitrogen. The mixture is heated at reflux for 22 h, is allowed to cool and the solvent is evaporated under reduced pressure. The residue is purified by chromatography on a column of silica gel, the eluent being a 100/0 to 85/15 dichloromethane/methanol mixture, and the solid obtained is recrystallized from ethyl acetate. 0.96 g (0.0027 mol) of base is obtained.

The fumarate is prepared from 0.96 g of base in solution in 50 ml of methanol and from 0.31 g (0.0027 mol) of fumaric acid in solution in 50 ml of methanol. The mixture is concentrated under reduced pressure and the product crystallizes. 0.97 g of white solid is obtained.

Melting point: 220°–222° C.

EXAMPLE 4 (COMPOUND NO. 12)

2-[[3-[4-(2-Cyclopropylphenyl)piperazin-1-yl]propyl]-methylamino]pyrazine-5-carboxamide (E)-but-2-enedioate (1:1)

4.1.
3-[4-(2-Cyclopropylphenyl)piperazin-1-yl)-N-methyl-propanamine trihydrochloride.

9.0 g (0.0444 mol) of 1-(2-cyclopropylphenyl)piperazine, 200 ml of dimethylformamide, 17.5 g (0.0444 mol) of 3-bromo-N-methyl-N-(triphenylmethyl)propanamine and 9 g of potassium carbonate are introduced into a 500 ml round-bottomed flask equipped with a reflux condenser and placed under nitrogen, and the mixture is heated three times for 6 h at 96° C. The solvent is evaporated under reduced pressure, the residue is taken up with water and dichloromethane, the organic phase is separated, washed with water, dried over sodium sulphate and the solvent is evaporated under reduced pressure. There are obtained 4.17 g of 3-[4-(2-cyclopropylphenyl)piperazin-1-yl]-N-methyl-N-(tri-phenylmethyl)-propanamine in the form of an oil which is dissolved in 200 ml of methanol, a stream of gaseous hydrochloric acid is passed therein for 10 min, the mixture is concentrated, allowed to stand for 2 days and the precipitate is separated by filtration. 2.94 g of compound are obtained.

4.2.
2-[[3-[4-(2-Cyclopropylphenyl)piperazin-1-yl]propyl]-methylamino]pyrazins-5-carboxamide (E)-but-2-enedioate (1:1)

3.77 g (0.0138 mol) of 3-[4-(2-cyclopropylphenyl)piperazin-1-yl]-N-methylpropanamine, 2.17 g (0.0138 mol) of 2-chloropyrazine-5-carboxamide, 1.9 g (0.0138 mol) of potassium carbonate and 100 ml of acetonitrile are introduced into a 500 ml round-bottomed flask, equipped with a reflux condenser and placed under nitrogen, and the mixture is heated at reflux for 18 h, allowed to cool, the solvent is evaporated under reduced pressure and the residue purified by chromatography on a column of silica gel, the eluent being a 100/0 to 90/10 dichloromethane/methanol mixture. The solid obtained is recrystallized from ethyl acetate and 2.37 g (0.006 mol) of base are obtained.

The fumarate is prepared from 2.37 g of base in solution in 50 ml of methanol and from 0.7 g (0.006 mol) of fumaric acid in solution in 50 ml of methanol. The mixture is concentrated under reduced pressure and the product crystallizes. 1.7 g of white solid are obtained.

Melting point: 184°–186° C.

EXAMPLE 5 (COMPOUND NO. 10)

2-[[3-[4-(5-Chloro-2-methoxyphenyl)piperazin-1-yl]propyl]amino]pyrazine-5-carboxamide (E)-but-2-enedioate (1:1)

5.1. 2-[3-[4-(5-Chloro-2-methoxyphenyl) piperazin-1-yl]propyl]-1H-isoindole-1,3(2H)-dione 17.16 g (0.05236 mol) of 1-(5-chloro-2-methoxyphenyl) piperazine (E)-but-2-enedioate (1:1), 14.04 g (0.05236 mol) of 2-(3-bromopropyl)-1H-isoindole-1,3(2H)-dione and 7.24 g (0.05236 mol) of potassium carbonate in suspension in 150 ml of dimethylformamide are introduced into a 500 ml round-bottomed flask and the mixture is heated for 4 h at 90° C.

The reaction mixture is poured onto 300 ml of water and extraction is carried out with ethyl acetate (2×150 ml). The organic phase is washed with water (3×150 ml) and is then dried over sodium sulphate, filtration is carried out and the solvents are evaporated under reduced pressure. The crude residue is recrystallized from diethyl ether and 14.7 g of solid are obtained.

Melting point: 130°–131° C.

5.2. 3-[4-(5-Chloro-2-methoxyphenyl)piperazin-1-yl]-propanamine 19.7 g (0.05105 mol) of 2-[3-[4-(5-chloro-2-methoxyphenyl)piperazin-1-yl]propyl]-1H-isoindole-1,3(2H)-dione in solution in 300 ml of ethanol are placed in a 1 l round-bottomed flask, 5.11 g (0.1021 mol) of hydrazine hydrate are then added and the mixture is heated at the reflux temperature for 4h.

The solvent is evaporated under reduced pressure, 100 ml of water and 17 ml of concentrated hydrochloric acid are then added to the crude residue and heating is again carried out at the reflux temperature of the solvent for 3 h.

The insoluble material is separated by filtration and the filtrate is basified with 30% sodium hydroxide solution and then extracted with dichloromethane. The organic phase is washed with water, dried over sodium sulphate, filtered and then the solvents are evaporated under reduced pressure in order to obtain 13.76 g of oil which is used as is in the following stage.

5.3.
2-[[3-[4-(5-Chloro-2-methoxyphenyl)piperazin-1-yl]propyl]amino]pyrazine-5-carboxamide (E)-but-2-enedioate (1:1)

13.67 g (0.04817 mol) of 3-[4-(5-chloro-2-methoxyphenyl)piperazin-1-yl]propanamine, 8.65 g (0.062 mol) of potassium carbonate and 7.59 g (0.04817 mol) of 2-chloropyrazine-5-carboxamide in suspension in 200 ml of dimethylformamide are introduced into a 500 ml round-bottomed flask and the mixture is stirred at room temperature for 48 h.

The solvent is evaporated under reduced pressure, the residue is purified by recrystallization from ethyl acetate and 12.6 g of base are obtained.

The fumarate is prepared from 1.58 g (0.0039 mol) of base in 50 ml of ethanol and from 0.47 g (0.0039 mol) of fumaric acid in 50 ml of ethanol. The mixture is concentrated and the product recrystallized from a methanol/ethanol mixture. 1.08 g (0.00207 mol) of white solid are finally obtained.

Melting point=219°–223° C. (decomposition).

EXAMPLE 6 (COMPOUND NO. 13)

1,1-Dimethylethyl 2-[[[2-[[3-[4-(5-chloro-2-methoxyphenyl)piperazin-1-yl]propyl]amino]pyrazin-5yl]carbonyl]amino]ethylcarbamate

6.1. Methyl 2-[[3-[4-(5-chloro-2-methoxyphenyl)piperazin-1-yl]propyl]amino]pyrazine-5-carboxylate.

9.7 g (0.024 mol) of 2-[[3-[4-(5-chloro-2-methoxyphenyl)piperazin-1-yl]propyl]amino]pyrazine-5-carboxamide are introduced into 400 ml of methanol in a 1 l round-bottomed flask, a stream of gaseous hydrochloric acid is then passed for a few minutes and heating is carried out at the reflux temperature of the methanol for 5 h.

The solvent is evaporated under reduced pressure, 200 ml of dichloromethane are added to the residue and the mixture is cooled to 0° C. The mixture is basified with a saturated aqueous sodium hydrogencarbonate solution, separation is carried out by settling and the organic phase is dried over sodium sulphate, filtered and the solvent is then evaporated under reduced pressure.

After chromatography on a silica column (eluent: 100/0 to 90/10 dichloromethane/methanol mixture) and then recrystallization from cyclohexane, 8.47 g (0.020 mol) of compound are isolated.

Melting point: 120°–122° C.

6.2 1,1-Dimethylethyl 2-[[[2-[[3-[4-(5-chloro-2-methoxyphenyl)piperazin-1-yl]propyl]amino]pyrazin-5-yl]carbonyl]amino]ethylcarbamate.

4 g (0.0095 mol) of methyl 2-[[3-[4-(5-chloro-2-methoxyphenyl)piperain-1-yl]propyl]amino]-pyrazine-5-carboxylate and 3.05 g (0.02 mol) of 1,1-dimethylethyl 2-aminoethylcarbamate are introduced into 10 ml of 2-propanol in a 0.5 l round-bottomed flask and the mixture is heated at reflux for 2 days.

The solvent is evaporated under reduced pressure and purification is carried out by chromatography on a column of silica gel (eluent: 100/0 to 90/10 dichloromethane/methanol) in order to obtain a yellow oil which crystallizes by trituration in diethyl ether. 1.5 g (0.00274 mol) of compound are finally isolated.

Melting point: 159°–161° C.

EXAMPLE 7 (COMPOUND NO. 14)

N-(2-Aminoethyl) -2-[[3-[4-(5-chloro-2-methoxyphenyl)-piperazin-1-yl]propyl]amino]pyrazine-5-carboxamide 2 g (0.00365 mol) of 1,1-dimethylethyl 2-[[[2-[[3-[4-(5-chloro-2-methoxyphenyl)piperazin-1-yl]propyl]amino]-pyrazin-5-yl]carbonyl]amino]ethylcarbamate are introduced into 10 ml of water in a 0.25 l round-bottomed flask and then 10 ml of concentrated hydrochloric acid are introduced dropwise. The mixture is cooled to 0° C. with an ice/salt/water mixture and 30% sodium hydroxide solution is added portionwise until the pH is basic. Extraction is carried out with dichloromethane, the organic phase is dried over sodium sulphate, filtered and the solvents are evaporated under reduced pressure and 1.32 g (0.00295 mol) of amorphous solid are obtained.

Melting point: 45°–55° C.

EXAMPLE 8 (COMPOUND NO. 15)

N-[2 -[[4-(Aminocarbonyl)pyrimidin-2-yl]amino]ethyl]-2-[[3- [4-(5-chloro-2-methoxyphenyl)piperazin-1-yl]propyl ]amino]pyrazine-5-carboxamide 1.32 g (0.00295 mol) of N-(2-aminoethyl)-2-[[3-[4-(5-chloro-2-methoxyphenyl)piperazin-1-yl]propyl]amino]-pyrazine-5-carboxamide, 0.5 g (0.00317 mol) of 2-chloropyrimidine-4-carboxamide and 0.6 g (0. 00434 mol) of potassium carbonate are introduced into 50 ml of dimethylformamide in a 0.25 l round-bottomed flask and the mixture is heated at 40° C. for 40 h.

The solvent is evaporated under reduced pressure and the crude residue is purified by chromatography on a column of silica gel, the eluent being a 98/2 to 80/20 dichloromethane/methanol mixture. After recrystallization from acetonitrile, 0.99 g (0.00174 mol) of compound is finally obtained.

Melting point: 197°–199° C.

The following table illustrates the chemical structures and the physical properties of some compounds according to the invention.

TABLE

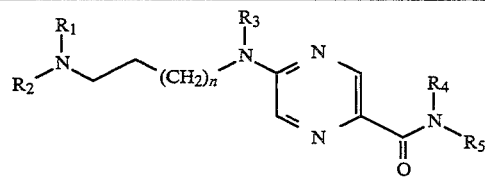

(I)

| No. | —NR₁R₂ | R₃ | R₄ | R₅ | n | Salt | M.p. (°C.) |
|---|---|---|---|---|---|---|---|
| 1 | (structure) | H | H | H | 1 | fum. | 161–163 |
| 2 | (structure) | H | H | H | 1 | fum. | 153–155 |
| 3 | (structure) | H | H | H | 1 | HCl | 218–220 |

TABLE-continued $$\text{(I)}\quad \underset{R_2}{\overset{R_1}{N}}{-}\text{CH}_2\text{CH}_2{-}(CH_2)_n{-}\underset{}{\overset{R_3}{N}}{-}\underset{\underset{O}{\overset{\|}{C}}{-}\underset{R_5}{\overset{R_4}{N}}}{\underset{\diagdown N \diagup}{\diagup N \diagdown}}$$

| No. | —NR₁R₂ | R₃ | R₄ | R₅ | n | Salt | M.p. (°C.) |
|---|---|---|---|---|---|---|---|
| 4 | 2-OCH₃-phenyl-N(piperazine-N-CH₃) | H | H | H | 1 | fum. | 210–214 (d) |
| 5 | 2-OCH₃-phenyl-N(piperazine-N-CH₃) | H | H | H | 0 | fum. | 220–222 |
| 6 | 2-OC₂H₅-phenyl-N(piperazine-N-CH₃) | H | H | H | 1 | fum. | 224–226 |
| 7 | 2-OC₂H₅-phenyl-N(piperazine-N-CH₃) | CH₃ | H | H | 1 | fum. | 186–188 |
| 8 | 2,5-di-OCH₃-phenyl-N(piperazine-N-CH₃) | H | H | H | 0 | fum. | 166–168 |
| 9 | 2,5-di-OCH₃-phenyl-N(piperazine-N-CH₃) | H | H | H | 1 | fum. | 210–212 |
| 10 | 5-Cl-2-OCH₃-phenyl-N(piperazine-N-CH₃) | H | H | H | 1 | fum. | 219–223 (d) |

TABLE-continued (I)

| No. | —NR₁R₂ | R₃ | R₄ | R₅ | n | Salt | M.p. (°C.) |
|---|---|---|---|---|---|---|---|
| 11 | 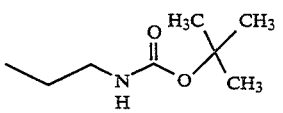 | H | H | H | 1 | fum. | 177–179 |
| 12 | 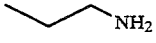 | CH₃ | H | H | 1 | fum. | 184–186 |
| 13 | 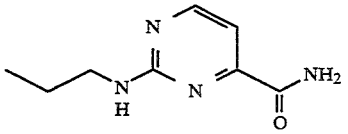 | H | H | $\underset{H}{N}\underset{\parallel}{\overset{O}{C}}O-C(CH_3)_3$ propyl carbamate | 1 | — | 159–161 |
| 14 | (same as 13) | H | H | propyl-NH₂ | 1 | — | 45–55 |
| 15 | (same as 13) | H | H | propylamino-pyrimidine-carboxamide | 1 | — | 197–199 |
| 16 | (same as 13) | H | H | propylamino-pyrazine-carboxamide | 1 | — | 194–196 |

Legend
In the "Salt" column, "fum." denotes an (E)-but-2-enedioate (1:1) (fumarate), "HCl" denotes a hydrochloride (1:1) and "—" denotes a compound in the base form. In the "M.p. (°C.)" column, "(d)" denotes a melting point with decomposition.

The compounds of the invention were made the subject of studies regarding their antagonist activity of $\alpha_1$-adrenergic receptors at the level of the lower urinary apparatus.

Their in vitro activity was studied on isolated rabbit urethra.

Adult male rabbit urethra rings are prepared according to the method of Ueda et al., Eur. J. Pharmacol., (1984), 103, 249–254, and then, after sensitization to noradrenalin, the concentration-response curve to phenylephrine is determined in the absence and in the presence of the compound to be studied.

The strength of the $\alpha_1$-adrenergic antagonism of each compound is evaluated by calculation of the pA₂, the antilogarithm of the molar concentration of the antagonist in the presence of which the concentration of the agonist must be doubled to cause the same effect as in its absence.

The $pA_2$ values of the compounds are between 7 and 10.

The in vivo activity of the compounds of the invention was studied with regard to their effect on the urethral hypertonia caused by the stimulation of the sympathetic fibres of the hypogastric nerve in anaesthetized cats.

Adult male cats are anaesthetized with sodium pentobarbital and they are prepared according to the method of Theobald, J. Auton. Pharmac., (1983), 3, 235–239, in order to obtain a urethral hypertonia by stimulation of the sympathetic fibres of the hypogastric nerve. The contractile responses of the urethra to the electrical stimulation of the hypogastric nerve are recorded before and after intravenous administration of the compounds to be studied, at cumulative doses from 1 to 1000 μg/kg.

The strength of the $α_1$-adrenergic antagonism of each compound is evaluated by calculation of the $ID_{50}$, the dose which inhibits urethral hypertonia by 50%.

The $ID_{50}$ values of the compounds of the invention are between 0.001 and 1 mg/kg.

The results of the tests show that the compounds of the invention show, in vitro, an antagonist activity of the $α_1$-adrenergic receptors of the smooth muscles of the lower urinary apparatus (urethra) stimulated by an $α_1$-adrenergic agonist (phenylephrine). In vivo they inhibit the urethral hypertonia caused by sympathetic nervous stimulation.

The compounds of the invention can thus be used for the symptomatic treatment of diseases and complaints which involve a hyperactivity of the α-adrenergic system at the level of the lower urinary apparatus, and especially for the treatment of urinary disorders of benign hypertrophy of the prostate, such as dysuria and pollakiuria.

To that end, they can be introduced in all forms appropriate for enteral or parenteral administration, combined with pharmaceutical excipients, for example in the form of tablets, sugar-coated pills, capsules, including gelatin capsules, drinkable or injectable solutions or suspensions, or suppositories, the quantities being such as to allow a daily dose of 0.1 to 500 mg of active substance.

We claim:

1. Compound corresponding to the formula (I)

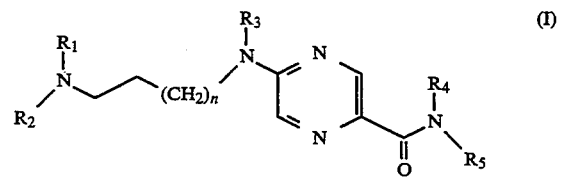

in which n represents the number 0 or 1, $R_1$ represents a methyl group, $R_2$ represents a phenoxy($C_1$–$C_4$)alkyl group in which the phenoxy group optionally carries 1 or 2 substituents selected from the group consisting of halogen atoms, methoxy groups and ethoxy groups, or $R_1$ and $R_2$ together form, with the nitrogen atom to which they are attached, a 4-(phenoxymethyl)piperid-1-yl group in which the phenoxy group optionally carries 1 or 2 $C_1$–$C_4$ alkyl groups or a 4-phenylpiperazin-1-yl group in which the phenyl group optionally carries 1 or 2 substituents selected from the group consisting of halogen atoms, methoxy groups, ethoxy groups, cyclopropyl and $C_1$–$C_4$ alkyl groups, $R_3$ represents a hydrogen atom or a methyl group, $R_4$ represents a hydrogen atom, $R_5$ represents a hydrogen atom or a group of general formula

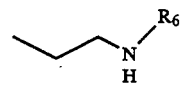

$R_6$ being a hydrogen atom, a tert-butyloxycarbonyl group, a 4-carbamoylpyrimidin-2-yl group or a 5-carbamoylpyrazin-2-yl group, as the free base or a pharmaceutically acceptable addition salt thereof.

2. A compound according to claim 1 in which n is 1, $R_3$ is hydrogen or methyl, $R_4$ is hydrogen, and $R_5$ is hydrogen.

3. A compound according to claim 1 in which —$NR_1R_2$ is a 4-phenylpiperazinyl group in which the phenyl carries 1 or 2 substituents chosen from chlorine, methoxy, and cyclopropyl.

4. Pharmaceutical composition, comprising a compound according to claim 1, in combination with a pharmaceutically acceptable excipient.

5. Method for the treatment of diseases and complaints which involve a hyperactivity of the α-adrenergic system at the level of the lower urinary apparatus which comprises administering to a subject in need of such treatment an effective amount of a compound according to claim 1.

* * * * *